United States Patent
Hargrove, Jr.

(10) Patent No.: US 7,667,215 B2
(45) Date of Patent: Feb. 23, 2010

(54) METHOD AND APPARATUS FOR PROVIDING RADIATION SHIELDING FOR NON-INVASIVE INSPECTION SYSTEMS

(75) Inventor: Richard Oliver Hargrove, Jr., Castro Valley, CA (US)

(73) Assignee: Morpho Detection, Inc., Newark, CA (US)

( * ) Notice: Subject to any disclaimer, the term of this patent is extended or adjusted under 35 U.S.C. 154(b) by 393 days.

(21) Appl. No.: 11/614,095

(22) Filed: Dec. 21, 2006

(65) Prior Publication Data

US 2008/0149864 A1 Jun. 26, 2008

(51) Int. Cl.
*G21F 3/00* (2006.01)
*H01J 35/16* (2006.01)

(52) U.S. Cl. ............. 250/515.1; 250/517.1; 250/519.1; 250/505.1; 378/203; 378/208

(58) Field of Classification Search ............. 250/359.1, 250/453.11, 455.11, 491.1, 492.1, 515.1, 250/517.1, 519.1, 505.1; 378/68, 69, 55, 378/203, 208; 198/502.1, 860.1, 950
See application file for complete search history.

(56) References Cited

U.S. PATENT DOCUMENTS

| | | | |
|---|---|---|---|
| 2,718,598 | A | 9/1955 | Graf |
| 2,807,699 | A * | 9/1957 | Moore ........................ 219/775 |
| 3,967,129 | A | 6/1976 | Winkler |
| 3,980,889 | A | 9/1976 | Haas et al. |
| 4,581,538 | A * | 4/1986 | Lenhart .................... 250/519.1 |
| 4,977,585 | A | 12/1990 | Boyd |
| 6,278,125 | B1 | 8/2001 | Belek |
| 6,304,629 | B1 * | 10/2001 | Conway et al. ................ 378/68 |
| 7,099,427 | B2 | 8/2006 | Cadwalader et al. |
| 2003/0205676 | A1 * | 11/2003 | Nelson et al. .......... 250/370.09 |
| 2008/0149864 | A1 * | 6/2008 | Hargrove ................. 250/515.1 |

FOREIGN PATENT DOCUMENTS

| | | |
|---|---|---|
| GB | 319940 A | 10/1929 |
| JP | 2006/343187 | 12/2006 |

OTHER PUBLICATIONS

"CTX 9000 DSi Automated Explosives Detection System", product description from website, http://www.gesecurity.com/portal/site/GESecurity/menuitem.f76d98ccce4cabed5efa421766030730?selectedID=2728&seriesyn=true&seriesID=.
"YxIon 3500 Explosives Detection System", product description from website, http://www.gesecurity.com/portal/site/GESecurity/menuitem.f76d98ccce4cabed5efa421766030730? selectedID=2942&seriesyn=true&seriesID=.
CTX 9000 DSi Product Brochure, http://www.gesecurity.com/portal/GESDownload?ID=2961&DID=16854&documenttype=Product%20Brochure.

* cited by examiner

*Primary Examiner*—Bernard E Souw
(74) *Attorney, Agent, or Firm*—Armstrong Teasdale LLP (57) ABSTRACT

Disclosed herein is a method and apparatus for providing radiation shielding for non-invasive inspection systems. An embodiment of the apparatus may include a radiation shield having a plurality of slats, where each of the plurality of slats comprises a radiation attenuating material. The radiation shield may further include a support structure configured to hold the slats in a non-planar shape. An embodiment of the method may include gathering a plurality of slats, each slat comprising a radiation attenuating material. The method may further include disposing the slats to form a shielding curtain having a non-planar shape. The method may also include positioning the shielding curtain to cover an opening of a scanner.

9 Claims, 6 Drawing Sheets

METHOD AND APPARATUS FOR PROVIDING RADIATION SHIELDING FOR NON-INVASIVE INSPECTION SYSTEMS

BACKGROUND

1. Field of the Invention

The technology disclosed herein relates to radiation shielding systems generally, and more particularly, to a method, apparatus, and system for providing radiation shielding for non-invasive inspection systems.

2. Discussion of Related Art

Explosive detection systems and other types of inspection systems typically use radiation-based scanners, such as x-ray line scanners, x-ray CT scanners, and coherent x-ray scatter scanners, to examine bags (pieces of passenger baggage) for the presence of one or more alarm objects (explosives, weapons, illegal drugs, contraband, product components, and the like). In certain types of inspection systems, such as explosive detection systems, one or more shielding curtains typically blocks the entrance and exit of an x-ray scanner, since highly concentrated dose of high-energy radiation from the scanner can damage human tissue if the dose is too high. Some shielding curtains (hereinafter, "sheet curtains") are formed of solid sections of material. More commonly, radiation-shielding curtains (hereinafter, "strip curtains") are formed of multiple adjoining slats, each of which is aligned with adjacent slats to form a common plane.

Figure 1:
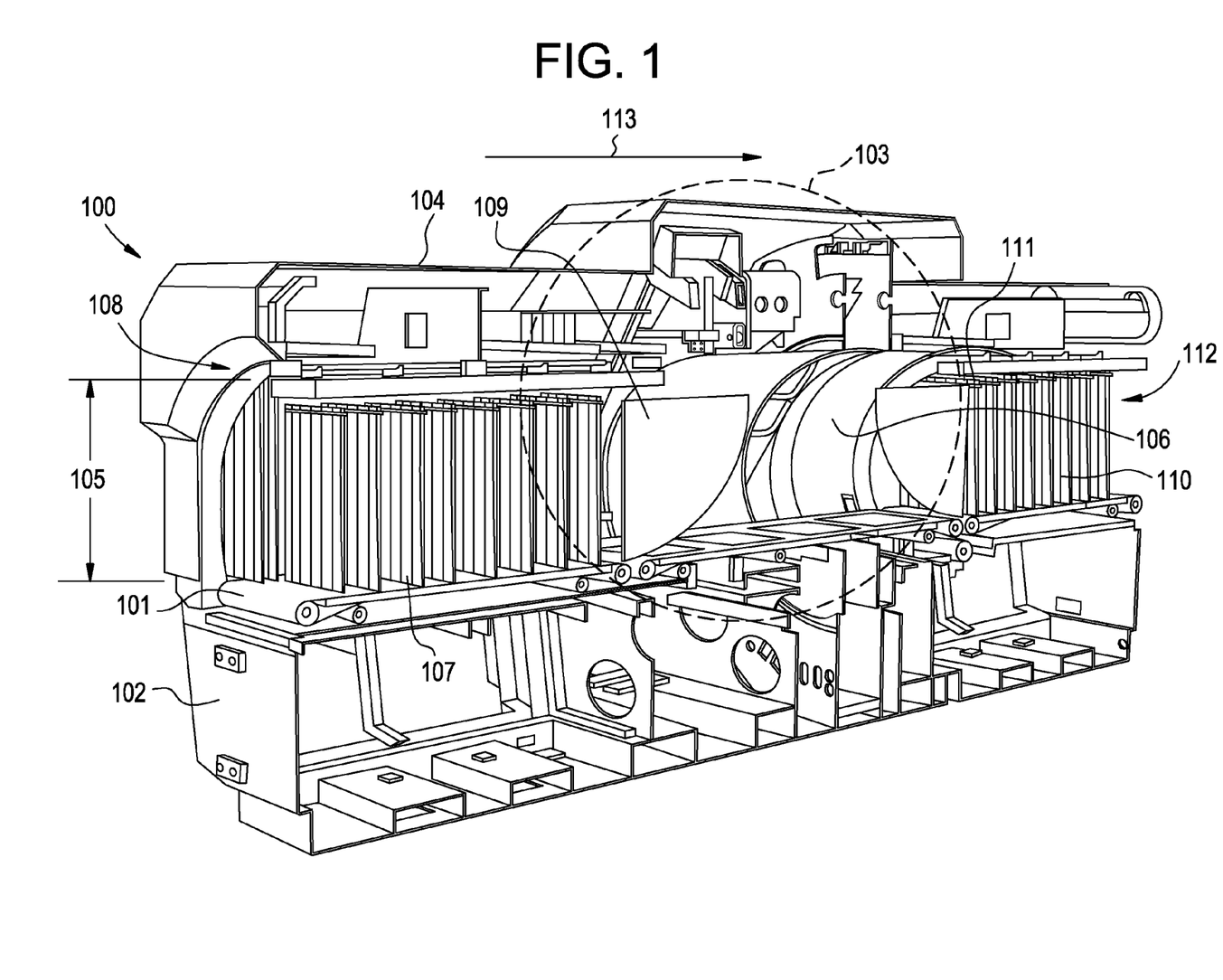
FIG. 1 is a sectional, perspective view of a conventional explosive detection system illustrating the layout and components of the explosive detection system.

FIG. 1, a sectional, perspective view of a conventional explosive detection system (EDS) 100, provides an example of how radiation-shielding curtains are typically arranged. In FIG. 1, a conveyor belt 101, positioned on a base 102, extends from one end of the EDS 100 to the opposite end of the EDS 100. The base 102 houses one or more conveyor belt motors (not shown), a computer (not shown), and one or more components of an x-ray scanner 103. A housing 104 rests on the base 102. A tunnel 105 formed in the housing 104 extends from one end of the housing 104 to the opposite end of the housing 104, and encloses the conveyor belt 101.

The x-ray scanner 103, positioned within a center portion of the housing 104, includes a scanning area 106, into which the conveyor belt 101 introduces one or more scannable objects. Configurations of the scanning area 106 will vary depending on the type of x-ray scanner used. For example, if an x-ray CT scanner is used, the scanning area 106 will be enclosed by a circular, movable gantry, to which an x-ray source and one or more detectors are fixedly attached.

Multiple, closely-spaced, strip curtains 107 hang suspended within the housing 104 over a portion of the conveyor belt 101. The portion of the conveyor belt over which the strip curtains 107 are positioned extends from an entrance 108 of the EDS 100 to an entrance 109 of the scanning area 106. In a like manner, parallel, planar rows of strip curtains 110 hang suspended within the housing 104 over another portion of the conveyor belt 101. This other portion of the conveyor belt 101 extends from the exit 111 of the scanning area 106 to the exit 112 of the housing 104.

In use, pieces of luggage (hereinafter, "bags") may be loaded onto the conveyor belt 101 at the entrance 108 of the tunnel 105. Supported by the conveyor belt 101, the bags proceed through the EDS 100 in the direction of arrow 113 (from the EDS 100 entrance 108 to the EDS 100 exit 112). Enroute through the EDS 100, each bag passes through the scanning area 106 and is scanned by the x-ray scanner 103. After being scanned, the bags are transported by the conveyor belt 101 to the EDS 100 exit 112 and ejected from the EDS 100.

Aligning strip curtains in a common plane in the conventional manner, as shown in FIG. 1, has disadvantages. Chief among such disadvantages is that bags occasionally jam as they pass through the shielding curtains. When shielding curtains are arranged in parallel, planar rows, jamming occurs because most or all of the slats will contact a bag simultaneously, which traps the bag(s) in the strip curtain(s) even though the conveyor belt supporting the bag(s) continues to move. Another disadvantage associated with conventional strip curtains, such as those illustrated in FIG. 1, is that the slats from one strip curtain often entangle the slats of one or more other strip curtains.

One or more solutions are needed, which attenuate radiation produced by a radiation-based scanner while simultaneously permitting objects to enter and exit the scanner without jamming.

BRIEF DESCRIPTION

Embodiments of the invention overcome the disadvantages associated with the related art and meet the needs discussed above. For example, embodiments of the invention provide a radiation shield, and configurations thereof, that permit bags or other scannable objects to enter and exit a radiation-based scanner without jamming, while simultaneously confining radiation to a scanning area of the scanner.

Relatively simple and cost-effective to manufacture and install, shielding curtains constructed and configured in accordance with embodiments of the present invention provide advantages that render them suitable for use in security applications, manufacturing applications, medical applications, etc. The solutions provided by such shielding curtains, and configurations thereof, afford several advantages, or technical effects. Illustratively, these advantages include, but are not limited to, significantly fewer bag jams, increased baggage throughput, reduced maintenance costs, and/or operating costs—all as compared with conventional shielding curtains and conventional shielding curtain configurations.

Embodiments of the invention increase baggage throughput by creating rows of non-planar passive shielding curtains. Each non-planar passive shielding curtains may comprise any suitable geometric shape. In one embodiment, each non-planar passive shielding curtain comprises slats of radiation-attenuating material arranged in a chevron-shape. The chevron configuration has at least two advantages. First, a chevron configuration reduces the number of slats that simultaneously contact a bag as the bag moves through the shielding curtain. The chevron configuration also reduces the force of the initial impact of the bag as it moves through the curtains and therefore reduces the occurrence of bag jams while still providing radiation protection. Reducing or eliminating the number of bag jams in this manner increases the number of bags a radiation-based inspection system can process in a given amount of time.

Many factors will affect the bag jam rate. Exemplary factors include, but are not limited to: whether the apex of the non-planar radiation shield is directed toward a scanning area or toward a portal through which bags enter or exit the scanner; the degree of the curtain angle; how many rows of shielding curtains will be used; how far apart the curtain rows are spaced from each other; and the height, weight, and width of the slats used to form each shielding curtain. In an embodiment of the invention, at least one or more of these exemplary factors is optimized to reduce the occurrence of bag jams.

Shielding curtains constructed and configured in accordance with embodiments of the invention may attenuate any known type of radiation. Non-limiting examples of the types of radiation that may be attenuated include: X-ray radiation, microwave radiation, laser radiation, and the like.

An embodiment of the invention provides a novel radiation shield. The radiation shield may include a plurality of slats, each comprised of a radiation attenuating material, and a support structure (or means for holding). The support structure (or means for holding) may be configured to hold the slats in a non-planar shape.

Another embodiment of the invention provides a method of constructing and/or installing a novel radiation shield. The method may include: gathering a plurality of slats, each comprised of a radiation attenuating material; disposing the slats to form a strip curtain having a non-planar shape; and positioning the strip curtain to cover an opening of a scanner.

The foregoing has outlined rather broadly the features of embodiments of the invention so that the following detailed description may be better understood. Additional features and advantages of various embodiments of the invention that form the subject matter of the appended claims are described below.

BRIEF DESCRIPTION OF THE DRAWINGS

For a more complete understanding of the technology described herein, and the advantages thereof, reference is now made to the following descriptions taken in conjunction with the accompanying drawings, in which.

DETAILED DESCRIPTION

Reference is made herein to the accompanying drawings briefly described above, which show by way of illustration various embodiments of the invention. Persons of ordinary skill in the above-referenced technological field will recognize that other embodiments may be utilized, and that various changes may be made without departing from the scope of the claimed invention.

As used herein, an element or step recited in the singular and proceeded with the word "a" or "an" includes plural elements or steps, unless exclusion of such plural elements or steps is explicitly recited.

Figure 2:
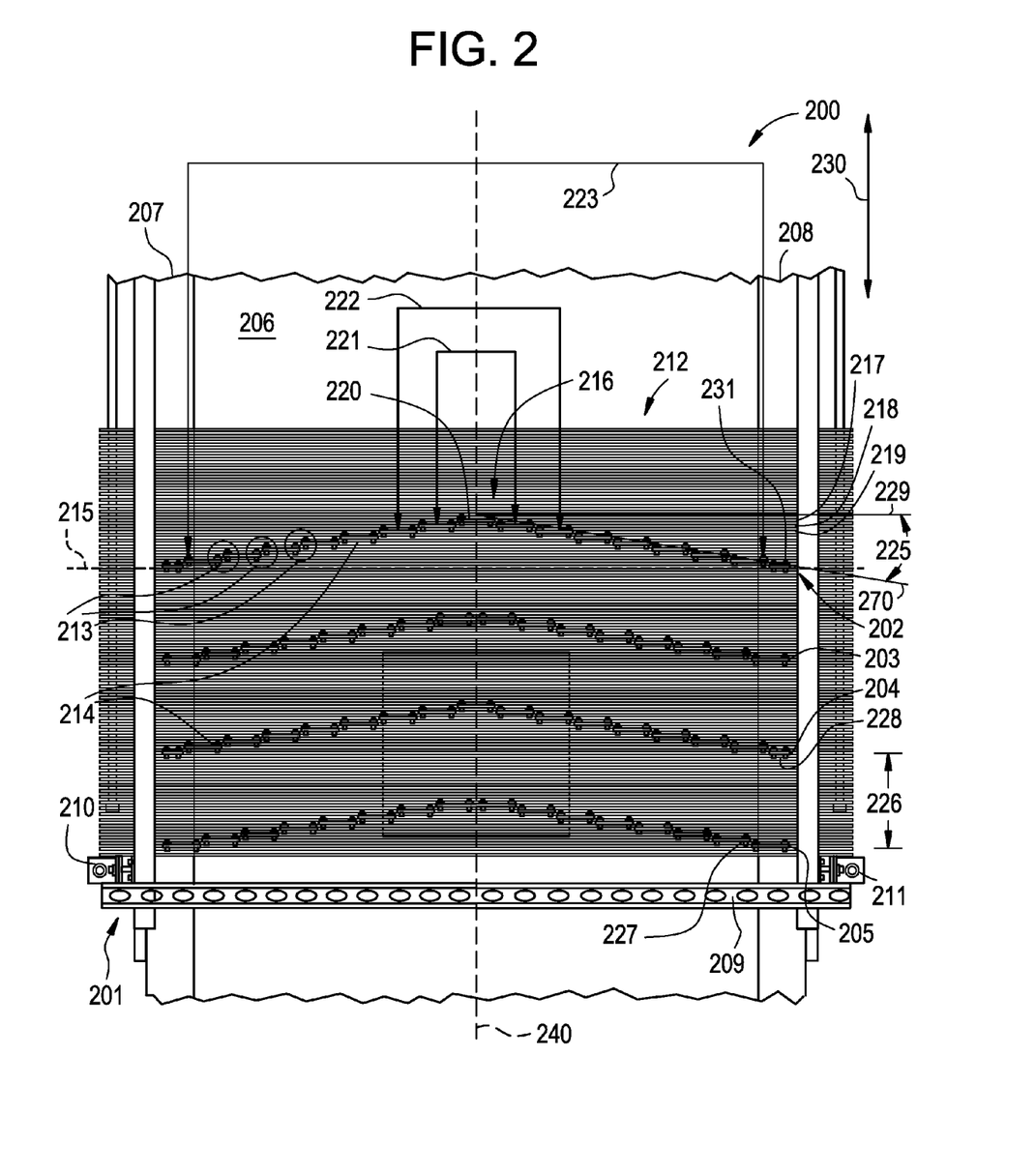
FIG. 2 is a top view of a radiation shield configured according to an embodiment of the invention.

FIG. 2 is a top view of an embodiment of a radiation shield having four strip curtains, each arranged in a non-planar shape. Any type of non-planar (e.g., three-dimensional) shape may be used, a non-limiting example of which is a chevron-shape. As used herein, "chevron-shape" refers to a "V," "U," inverted "V," or inverted "U" arrangement of radiation shielding material. As used herein, "radiation shield" refers to any configuration of radiation attenuating material configured to attenuate an amount of radiation leakage and/or scatter radiation that may occur during operation of a radiation-based scanner. The term "scanner" refers to any type of hardware and/or related software (i.e., linear x-ray, computed tomography (CT), coherent x-ray scatter, laser, magnetic resonance imaging (MRI), etc.) configured to generate a digital representation of an object for storage in a computer-readable medium and/or for analysis by a computer. The term "strip curtain" refers to a grouping of slats of radiation attenuating material. The term "radiation attenuating material" refers to any material that absorbs or reflects radiation including, but not limited to, aluminum, antimony, bismuth, barium, cadmium, copper, iron, iodine, lead, mercury, nickel, silver, thallium, tantalum, tellurium, tin, tungsten, uranium, and zinc, either alone or in combination. The term "slat" refers to a thin piece of radiation attenuating material having a length greater than its width.

Referring to FIG. 2, a radiation shield 200 includes a plurality of flexible (or semi-flexible) slats of radiation attenuating material 214, and means for holding the flexible slats 214 to form a strip curtain (202, 203, 204, and 205) having a non-planar shape. In an embodiment, the holding means comprises a frame 201 and a plurality of curtain supports 212 from which one or more non-planar strip curtains 202, 203, 204, 205 hang. In an airport security application or an engineering application, the non-planar strip curtains may be suspended over a conveyor belt 206, which may move objects in either direction indicated by the double-ended direction arrow 230. Also as used herein, "object" refers to anything that can be imaged by a scanner. Non-limiting examples of an "object" include a bag, a medical patient, a commercial product, etc. The term "bag" refers to a piece of baggage, and the term "baggage" refers to all of a traveler's luggage and personal belongings.

In a medical application, the non-planar strip curtains 212 may be suspended over a portion of a support structure that supports a medical patient (or a portion thereof). Non-limiting examples of a support structure include a bed, a table, a stretcher, a gurney, etc. As used herein, "gurney" refers to a mobile bed with wheels designed for transport of patients in hospitals and ambulances.

Referring again to FIG. 2, the frame 201 may include two substantially parallel, longitudinally extending beams 207 and 208. The beams 207,208 may be braced with one or more lateral support members 209. Any type of known means for fastening (e.g., a weld, a bolt, screw, etc.) can be used to couple the lateral support member(s) 209 with one of the beams 207 and 208. The frame 201 may further include two upright support members 210 and 211, which support the beams 207 and 208 above the conveyor belt 206.

The frame 201 may further include one or more curtain supports 212, which, in an embodiment, may be cylindrical rods that lie orthogonally across the beams 207 and 208. Each curtain support 212 may fixedly or adjustably couple with the beams 207 and 208. In turn, an upper end of each slat 214 may couple with one of the curtain supports 212 via one or more fasteners 213.

Each non-planar strip curtain 202, 203, 204 or 205 may include multiple curtain supports 212. For example, in one embodiment, each non-planar strip curtain 202, 203, 204, and 205 includes eight curtain supports 212. In other embodiments, the number of curtain supports 212 included in each non-planar strip curtain 202, 203, 204, and 205 may be greater or less than eight.

Each slat 214 may comprise any radiation attenuating material or combination of materials known to a skilled artisan. Such a material may have a unique radiation transmission attenuation factor, which will vary depending upon the specific embodiment. In an embodiment, the radiation attenuating material is generally flexible to permit each slat 214 to flex slightly when pushed by a bag. In alternative embodiments, the radiation attenuating material may be weighted and/or rigid.

Referring again to FIG. 2, each non-planar strip curtain 202, 203, 204, and 205 includes a base 215 and an apex 216. In an embodiment, the base 215 is formed by two co-planar slats, and the apex 216 is formed either by a single slat or by two co-planar slats. The base 215 is distinguished from the apex 216 in that the two co-planar slats that form the base 215 are separated by a greater lateral distance (as measured orthogonally to a longitudinal center axis 240) than the co-planar slat(s) that form the apex 216. Additionally, the base 215 is vertically separated (as measured along the longitudinal center axis 240) from the apex 216. When configured in this manner, each non-planar strip curtain 202, 203, 204, and 205 has a height (measured orthogonal to the conveyor belt 206), a width (measured parallel to a width of the conveyor belt 106), and a depth (measured along the longitudinal center axis 240 from a plane passing through the base slats to a plane passing through the apex slat(s)).

The chevron-shape of each strip curtain 202, 203, 204, and 205 is formed by arranging slats 214 in a predetermined pattern such that the slats 214 are generally longitudinally aligned (as measured along the longitudinal center axis 240) and laterally staggered (as measured orthogonal to the longitudinal center axis 240).

In an embodiment, "longitudinally aligned" refers to one of two arrangements of slats. In a first arrangement, the centers of slats in one shielding curtain are generally aligned with the centers of slats in a second (adjacent) shielding curtain. In a second arrangement, the centers of slats in one shielding curtain are offset from the centers of slats in a second (adjacent) curtain. This second (offset) arrangement staggers the gaps (if any) between the curtain slats from row to row to prevent the gaps from being aligned and therefore reduce radiation leakage.

In an embodiment, "laterally staggered" refers to one of two arrangements. In a first arrangement, the side edges of slats within a shielding curtain are overlapped with each other so that no gaps appear between neighboring curtain slats. In a second arrangement, the side edges of slats within a shielding curtain are not overlapped. In this second arrangement, the side edges of slats within a shielding curtain may be separated by a gap.

In other words, one or more slats 214 forming the apex 216 may be attached to a center portion of a first curtain support 217. A first pair of slats 221, comprised of two slats 214 that are laterally spaced at about equal distances from the longitudinal center axis 240 of the frame 201, may be coupled with a second curtain support 218, which longitudinally adjoins the first curtain support 217. A second pair of slats 222, comprised of two slats 214 that laterally spaced at greater distances from the longitudinal center axis 240 than the first pair of strip curtains 220, may be coupled with a third curtain support 219, and so on, until a final pair of slats 223 having the greatest lateral spacing from the longitudinal center axis 240 are coupled with a final curtain support 231. In an embodiment, the final curtain support 231 is separated from the first curtain support 217 by one or more curtain supports disposed therebetween.

As illustratively shown in FIG. 2, such an arrangement of slats causes a curtain angle 225 to be formed, which determines how sharply the base 215 of each strip curtain 202, 203, 204, 205 tapers to its apex 216. Two intersecting (imaginary) lines may define the curtain angle 225. The first line 229, which orthogonally intersects the longitudinal center axis 240, may be drawn tangent the apex 216. The second line 270, which passes through the intersection of the first line 229 and the longitudinal center axis 240, may be drawn generally along a sloping face of the non-planar strip curtain 202 to be tangent an outer edge of one of the pair of slats 223 that form the base 215. In an embodiment, an exemplary curtain angle is about 8.0 degrees, but in alternative embodiments, lesser and greater curtain angles may also be used.

Still referring to FIG. 2, one or more predetermined curtain spacings 226 may separate two or more of the non-planar strip curtains 202, 203, 204, and 205 from each other. The amount of each curtain spacing 226 will vary depending on the embodiment and the type of application. Illustratively, the curtain spacing 226 may be measured as the distance separating one base strip curtain 227 (in strip curtain 205) from another adjacent base strip curtain 228 (in strip curtain 204). In an embodiment, an exemplary curtain spacing 226 measures about 152.40 mm, but other curtain spacings are possible.

Referring now to FIGS. 1 and 2, the apexes 216 of all or some of the non-planar strip curtains 202, 203, 204, 205 may be directed toward a scanning chamber 106 of a scanner 103. In such an embodiment, the apexes 216 of all or some of the non-planar strip curtains 202, 203, 204, 205 may be located nearer the chamber 106 than the bases 215 of each non-planar strip curtain. In alternative embodiments, the apexes 216 of all or some of the non-planar strip curtains 202, 203, 204, 205 may be directed away from the scanning chamber 106 of the scanner 103. In such alternative embodiments, the bases 215 of all or some of the non-planar strip curtains 202, 203, 204, 205 may be located nearer the chamber 106 than the apexes 216 of all or some of the non-planar strip curtains 202, 203, 204, 205.

Figure 3:
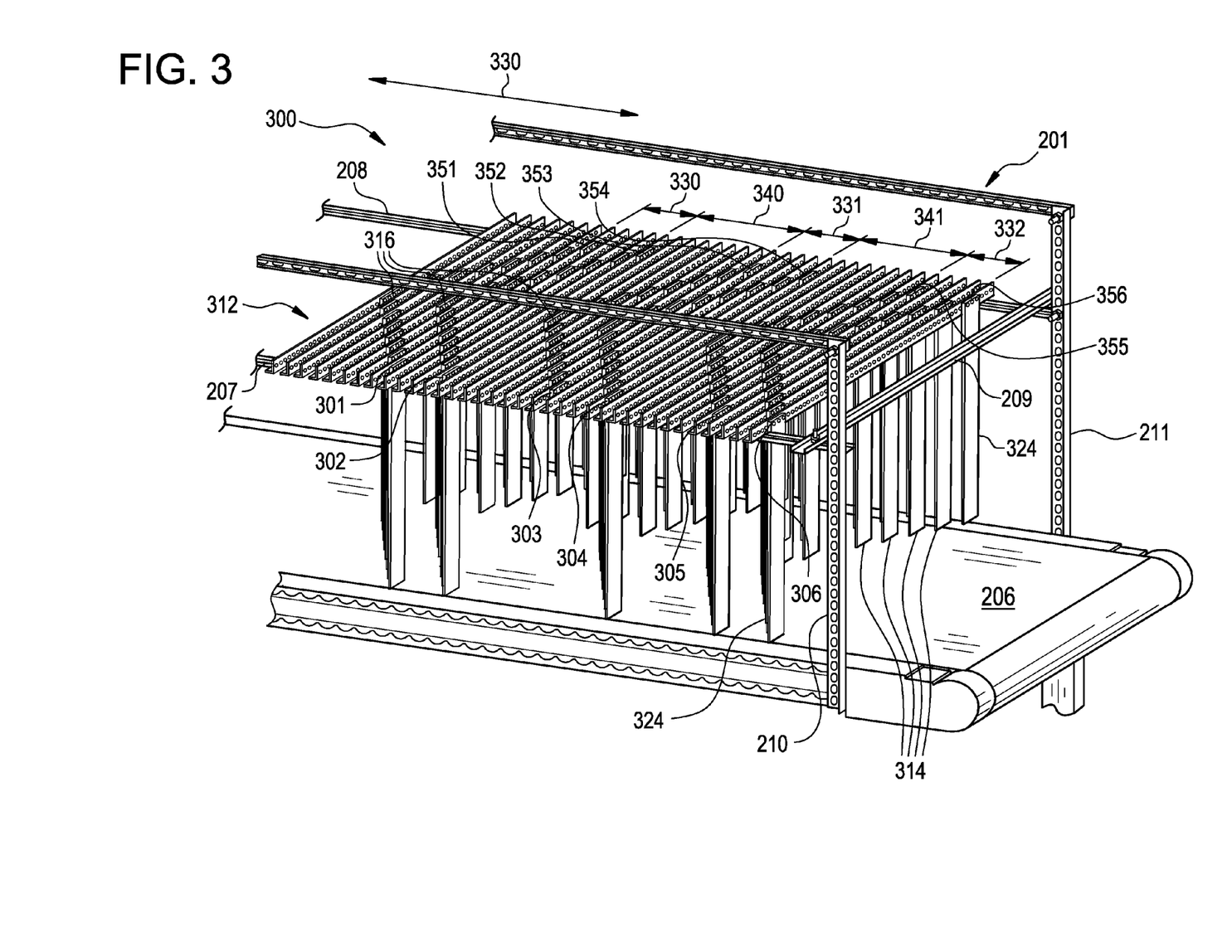
FIG. 3 is a perspective view of a radiation shield configured according to another embodiment of the invention.
Figure 4:
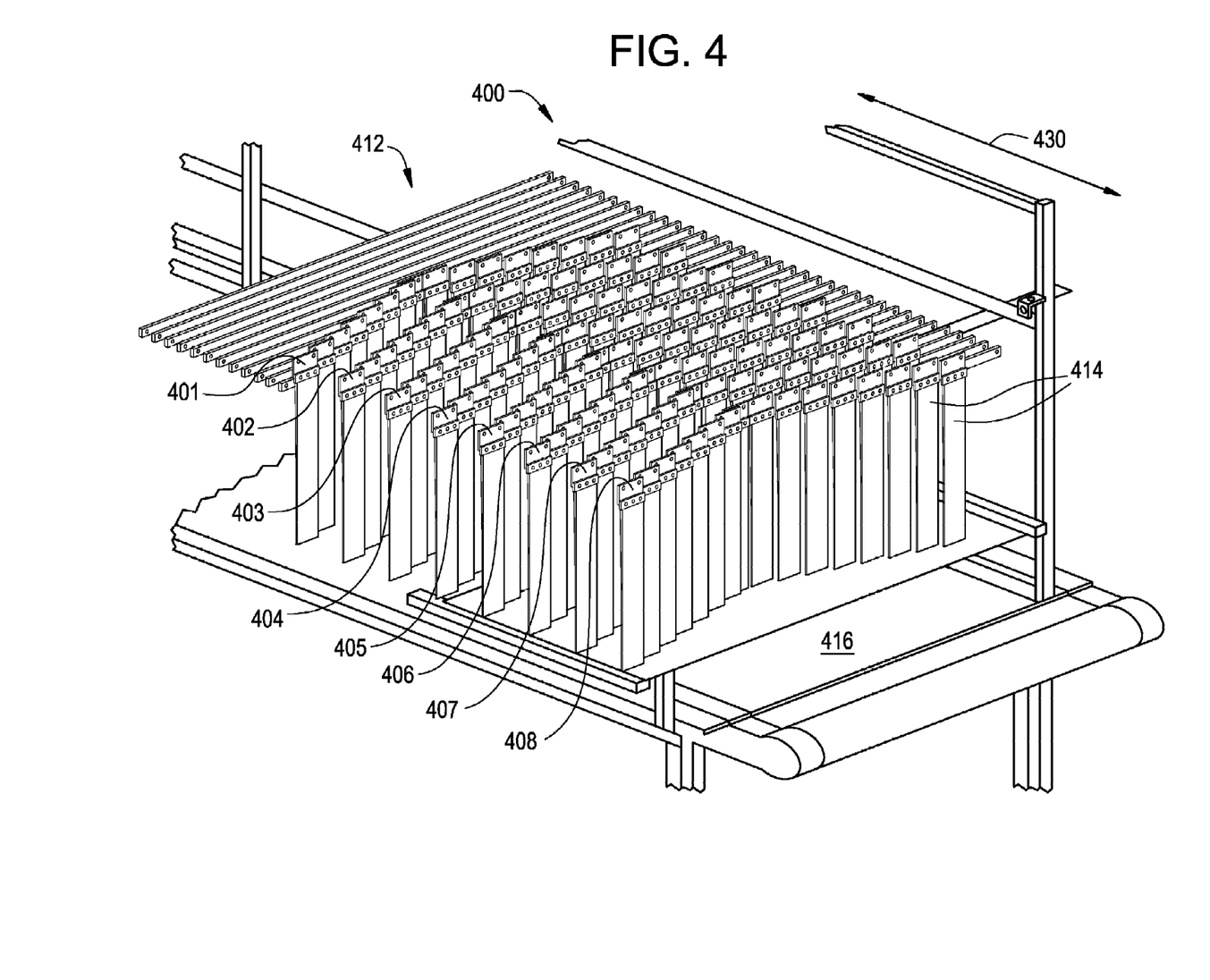
FIG. 4 is a perspective view of a radiation shield configured according to another embodiment of the invention.

FIGS. 3 and 4 are perspective views of embodiments of non-planar radiation shields 300 and 400, respectively. These views, as well as the top view shown in FIG. 2, illustrate exemplary frames and curtain supports, which allow quick changes from one curtain embodiment (or configuration) to another during testing. Skilled artisans will appreciate that various other means for supporting the novel configurations of shielding curtains described herein (for testing and/or use in an operational medical inspection system or explosive detection system) are possible and contemplated. FIG. 3 is a perspective view of a radiation shield 300 having six shielding curtains 301, 302, 303, 304, 305, 306, with each shielding curtain arranged in a chevron pattern, according to another embodiment of the invention. Each non-planar shielding curtain 301, 302, 303, 304, 305, 306 includes an apex 316 and a base 324, as previously described above with respect to FIG. 2.

In FIG. 3, the radiation shield 300 includes a frame 301 to which one or more curtain supports 312 are coupled. The six non-planar strip curtains 301, 302, 303, 304, 305, 306, each formed of one or more slats 314, hang suspended from the one or more curtain supports 312 over a conveyor belt 306 (or other type of means for supporting an object for scanning). The conveyor belt 306 may be configured to move objects in either direction indicated by the double-ended direction arrow 330.

The frame 201 may include two substantially parallel, longitudinal beams 307 and 308 that are braced with one or more lateral support members 309. The lateral support member(s) 309 are attached at either end to one of the beams 307 and 308 using any type of known fastening means (e.g., a weld, a bolt, screw, etc.). The frame 201 may further include two upright support members 310 and 311, which support the beams 307 and 308 above the conveyor belt 306. As noted above, the frame 201 may further include one or more adjustable or fixed curtain supports 312, which may fixedly or adjustably couple with the beams 307 and 308 at about right angles.

In the embodiment shown in FIG. 3, the non-planar strip curtains 301, 302, 303, 304, 305, 306 are paired into the following three groups: a first curtain pair consisting of strip curtains 301,302; a second curtain pair consisting of strip curtains 303,304; and a third curtain pair consisting of strip curtains 305,306. Each of these first, second, and third curtain pairs has an identical (or similar) internal curtain spacing 330, 331, and 332, respectively, which are further defined below. Additionally, each of the first, second, and third curtain pairs are separated from each other by spacings 340 and 341 (also defined further below). For example, spacing 340 separates the first curtain pair 301,302 from the second curtain pair 303,304. Another spacing 341 may separate the second curtain pair 303,304 from the third curtain pair 305,306.

In an embodiment, each of the internal curtain spacings 330, 331, and 332 that separate individual strip curtains are smaller than the spacings 340,341 that separate the first, second, and third curtain pairs.

The internal curtain spacings 330, 331, and 332 may be measured as follows. The internal curtain spacing 330 may be the distance between a base slat 351 of the strip curtain 301 and a base slat 352 of the strip curtain 302. The internal curtain spacing 331 may be the distance between a base slat 353 of the strip curtain 303 and a base slat 354 of the strip curtain 304. The internal curtain spacing 332 may be the distance between a base slat 355 of the strip curtain 305 and a base slat 356 of the strip curtain 306.

The spacings 340 and 341 between the first, second, and third curtain pairs may be measured as follows. The spacing 340 may be the distance between a base slat 352 of the strip curtain 302 and a base slat 353 of the strip curtain 303. The spacing 341 may be the distance between a base slat 354 of the strip curtain 304 and a base slat 355 of the strip curtain 305.

FIG. 4 is a perspective view of a radiation shield 400 having eight strip curtains 401, 402, 403, 404, 405, 406, 407, 408, with each strip curtain arranged in a chevron pattern that has a predetermined curtain angle, according to another embodiment of the invention. In FIG. 4, the eight non-planar shielding curtains 401, 402, 403, 404, 405, 406, 407, 408, each formed of a plurality of slats 414, are arranged on a plurality of curtain supports 412 that are coupled with a frame as described above. The slats 414 hang suspended above a conveyor belt 416, which may move objects in either direction indicated by the double-ended direction arrow 430. Additionally, the eight strip curtains 401, 402, 403, 404, 405, 406, 407, 408 are nested. As used herein, "nested" refers to an arrangement in which an apex of one strip curtain is positioned between a base and apex of another longitudinally aligned strip curtain, as illustratively shown in FIGS. 3 and 4. Depending on the embodiment, two or more strip curtains may be nested in single or multiple groupings. By way of example, FIG. 3 illustrates multiple groupings of nested pairs of strip curtains, while FIG. 4 illustrates a single grouping of nested strip curtains. On the other hand, the strip curtains illustrated in FIG. 2 would not be considered nested since the apex of each succeeding strip curtain is positioned outside of the base of the next adjacent strip curtain.

Figure 5:
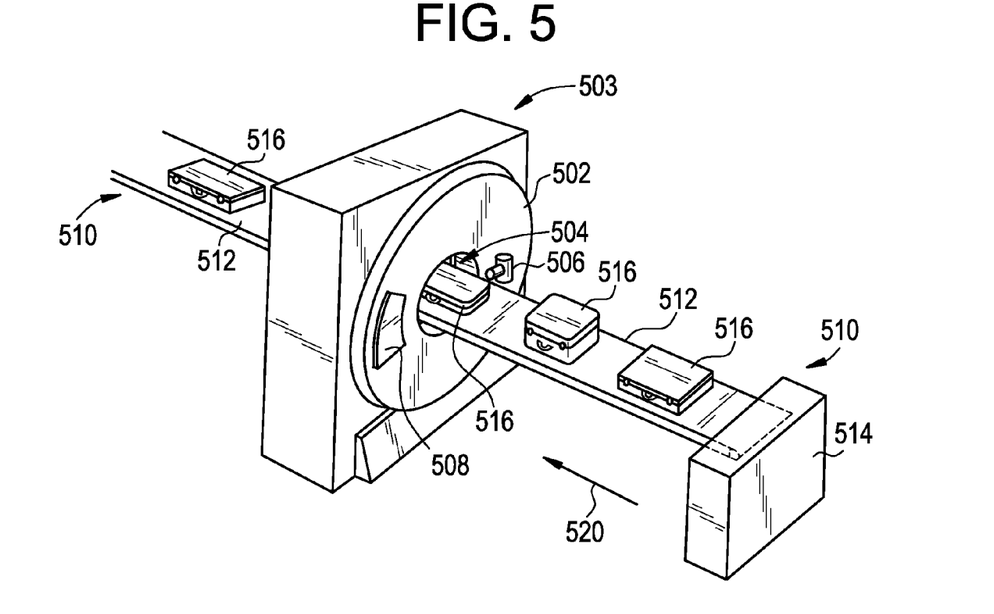
FIG. 5 is a perspective view of an exemplary x-ray based scanner for use with a non-invasive inspection system, which may be configured to include one or more non-planar radiation shields.

Referring now to FIG. 5, an example of an inspection system 500 is shown with its housing and shielding curtains removed for clarity. It will be appreciated that the embodiments of the non-planar strip curtains described herein may be positioned between the entrance 508 of the inspection system 500 and the scanner 503, and between the scanner 503 and the exit 518 of the inspection system 500.

The inspection system 500 may be configured to include one or more of the new non-planar shielding curtains described herein. The inspection system 500 includes a CT scanner 503 having a rotatable gantry 502. As used herein, "inspection system" refers to a machine having a scanner that scans an object to obtain scan data that is characteristic of the object (and/or its contents), and/or that analyzes the scan data using a computer to determine whether the object comprises and/or contains one or more alarm objects.

The rotatable gantry 502 has an opening 504 therein, through which packages or bags 516 may pass. The rotatable gantry 502 houses an x-ray source 506 as well as a detector assembly 508 having scintillator arrays comprised of scintillator cells. A conveyor system 510 is also provided. The conveyor system 510 includes a conveyor belt 512 supported by structure 514 to automatically and continuously pass packages or bags 516 to be scanned through opening 504. Directional arrow 520 indicates the direction in which the conveyor belt 512 rotates.

Objects 516 are fed through opening 504 by conveyor belt 512. Imaging data is then acquired, and the conveyor belt 512 transfers the packages 516 from the gantry opening 504 in a controlled and continuous manner. As a result, inspectors, baggage handlers, and other security personnel may non-invasively inspect the contents of packages 516 for alarm objects. The term "alarm object" refers to any substance or thing that an inspection system is configured to detect. Non-limiting examples of alarm objects include explosives, illegal drugs, hazardous substances, product components, and the like. Additional aspects of the inspection system 500 are described below with reference to FIGS. 5 and 6.

Figure 6:
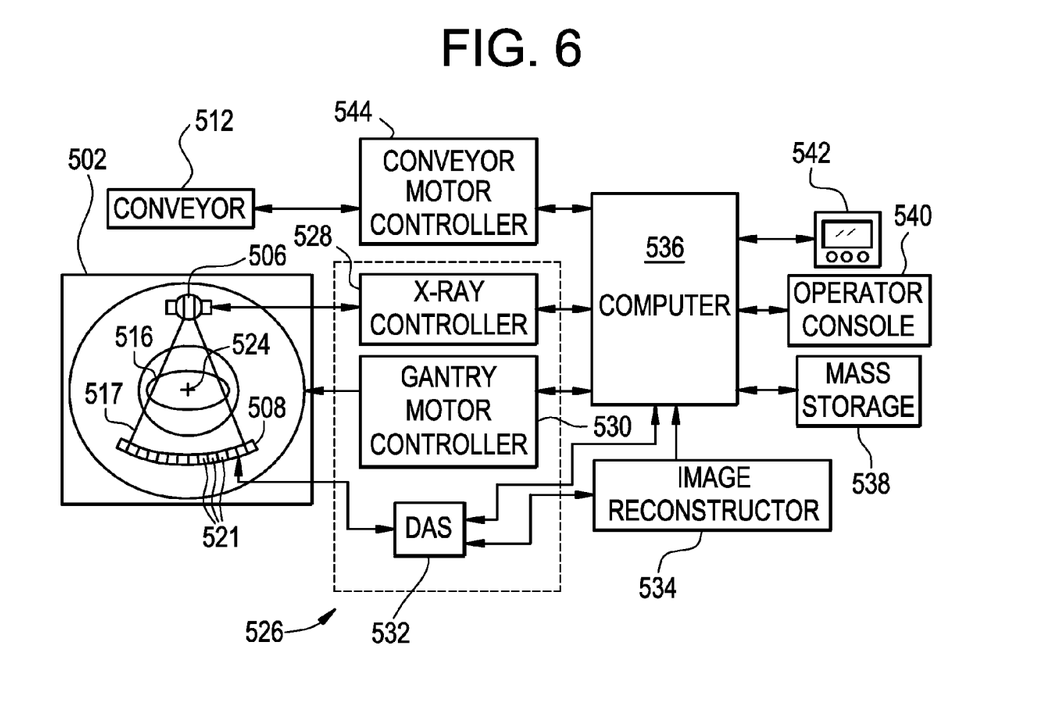
FIG. 6 is a block schematic diagram of a scanner that may be used in an inspection system, which is configured according to an embodiment of the invention.

FIG. 6 is a block schematic diagram of a scanner that may be used in an inspection system configured according to an embodiment of the invention. Referring to FIGS. 5 and 6 together, the inspection system 500 may be an explosive detection system that includes an x-ray CT scanner. As used herein, "explosive detection system" refers to a particular category of inspection system, configured to detect explosives in baggage.

Referring again to FIGS. 5 and 6, the x-ray CT scanner includes a circular, movable gantry 502. An x-ray source 506 attached to the gantry 502 projects a fan beam of x-rays 517 across the interior of the gantry 502 to a detector array 508 that is also attached to the gantry 502. The detector array 508 is formed by a plurality of detector modules 521, which together sense the projected x-rays that pass through an object 516. Each detector module 521 comprises an array of pixel elements (pixels). Each pixel comprises in part a photosensitive element, such as a photodiode, and one or more charge storage devices, such as capacitors. Each pixel produces an electrical signal that represents the intensity of an impinging x-ray beam and hence the attenuated beam as it passes through the object 516. During a scan to acquire x-ray projection data, gantry 502 and the components mounted thereon rotate about a center of rotation 524.

Rotation of gantry 502 and the operation of x-ray source 506 are governed by a control mechanism 526 of the inspection system 500. Control mechanism 526 includes an x-ray controller 528 that provides power and timing signals to an x-ray source 506 and a gantry motor controller 530 that controls the rotational speed and position of gantry 502. A data acquisition system (DAS) 532 in control mechanism 526 samples analog data from detectors 521 and converts the data to digital signals for subsequent processing. An image reconstructor 534 receives sampled and digitized x-ray data from DAS 532 and performs high-speed reconstruction. The reconstructed image is applied as an input to a computer 536, which stores the image in a mass storage device 538.

Computer 536 also receives commands and scanning parameters from an operator via console 540 that has a keyboard. An associated display 542 allows the operator to observe the reconstructed image and other data from computer 536. The operator supplied commands and parameters that are used by computer 536 to provide control signals and information to DAS 532, x-ray controller 528, and gantry motor controller 530. In addition, computer 536 operates a conveyor motor controller 544, which controls a conveyor belt 512 to position object 516 within the gantry 502. Particularly, conveyor belt 512 moves portions of the object 516 through the gantry opening 504.

Figure 7:
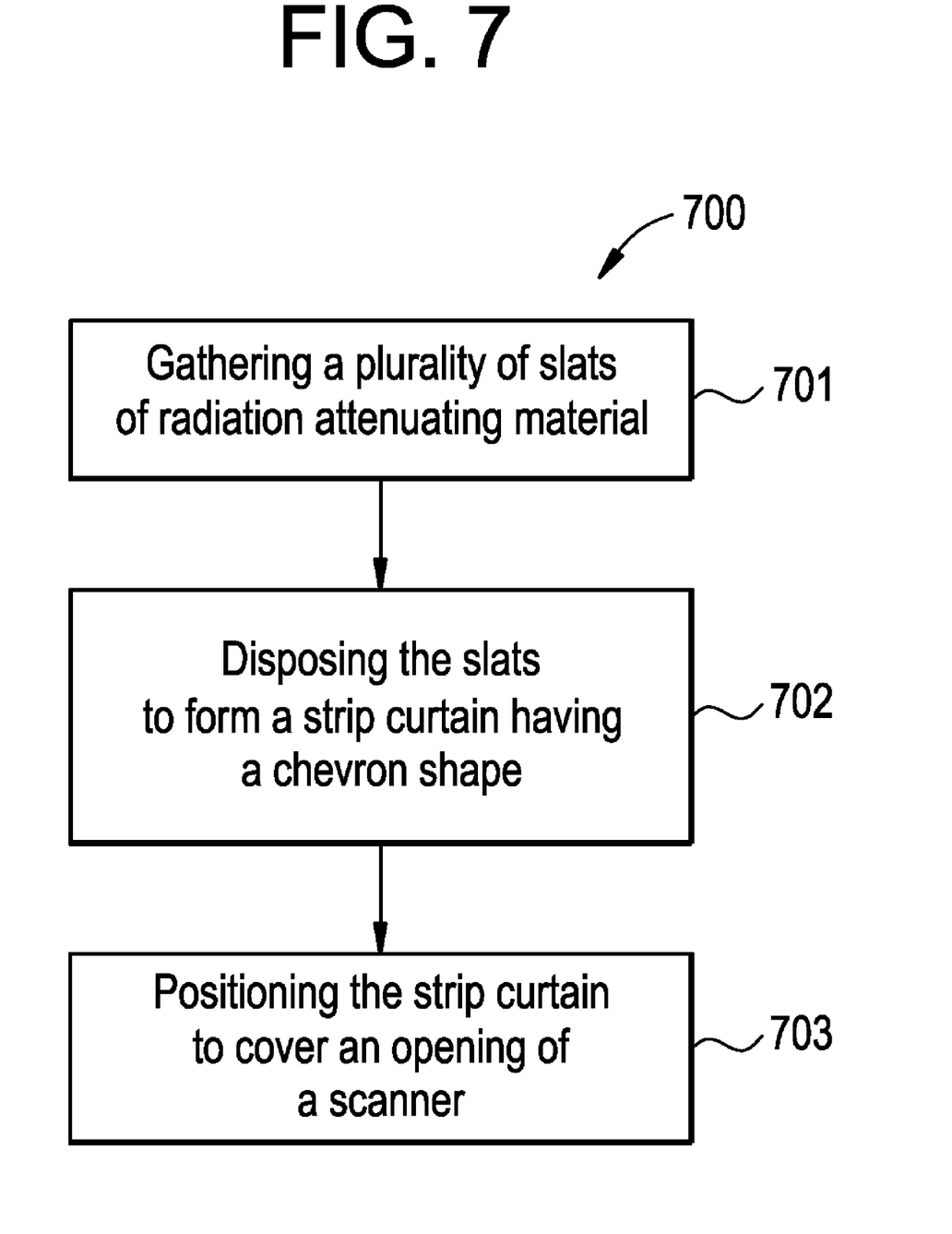
FIG. 7 is a flowchart of an embodiment of a method of constructing and configuring a radiation shield.

FIG. 7 is a flowchart of an embodiment of a method 700 of constructing a radiation shield. The method 700 may include a step 701 of gathering a plurality of slats of radiation attenuating material. The gathering step 701 may include ordering, constructing, and/or receiving one or more slats that each comprise a radiation attenuating material. The method 700 may further include a step 702 of disposing the slats to form a strip curtain having a non-planar shape. The step 702 may include one or more additional steps, such as, but not limited to: coupling each of the slats with a curtain support; coupling each curtain support with a frame, among other steps. The method 700 may further include a step 703 of positioning the strip curtain to cover an opening of a scanner. The opening of the scanner may be an entrance opening or an exit opening through which objects pass when traveling into or out of a scanning area of the scanner.

The construction and arrangement of the curtain shielding assembly, and/or an inspection system that includes an embodiment of the curtain shielding assembly, as described herein and shown in the appended figures, is illustrative only. Although only a few embodiments of the invention have been described in detail in this disclosure, those skilled in the art who review this disclosure will readily appreciate that many modifications are possible (e.g. variations in sizes, dimensions, structures, shapes and proportions of the various elements, values of parameters, mounting arrangements, use of materials, orientations, etc.) without materially departing from the novel teachings and advantages of the subject matter recited in the appended claims.

Accordingly, all such modifications are intended to be included within the scope of the present invention as defined in the appended claims. The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and omissions may be made in the design, operating conditions and arrangement of the preferred and other exemplary embodiments without departing from the spirit of the embodiments of the invention as expressed in the appended claims.

What is claimed is:

1. A radiation shield, comprising:
a frame (201);
a plurality of curtain supports (212) supported by the frame (201); and
a plurality of slats (214) coupled with the plurality of curtain supports (212) and arranged to form a first curtain (202) having a non-planar shape, each of the plurality of slats comprising a radiation attenuating material,
wherein the non-planar shape is defined in part by an apex (216) and a base (215), and
wherein the apex (216) is formed of at least one apex slat of the plurality of slats and the base (215) is formed of two co-planar base slats of the plurality of slats that are separated from the apex and also are laterally spaced apart from each other at about equal distances on either side of a center axis (240) that extends from a plane passing through the two base slats to a plane passing through the at least one apex slat,
wherein the at least one apex slat and each of the two base slats are substantially parallel.

2. The radiation shield of claim 1, wherein the non-planar shape is a chevron.

3. The radiation shield of claim 1, further comprising:
a second plurality of slats coupled with the plurality of curtain supports (212) and arranged to form a second curtain (203) having the non-planar shape wherein the second plurality of slats are longitudinally aligned with the plurality of slats, each of the second plurality of slats comprising a radiation attenuating material.

4. An inspection system, comprising:
a scanner;
a conveyor configured to move objects through the scanner; and a radiation shield positioned at an opening of the scanner, wherein the radiation shield comprises:
a frame (201);
a plurality of curtain supports (212) supported by the frame (201); and
a plurality of slats (214) coupled with the plurality of curtain supports (212) and arranged to form a first curtain (202) having a non-planar shape, each of the plurality of slats comprising a radiation attenuating material,
wherein the non-planar shape is defined in part by an apex (216) and a base (215), and wherein the apex (216) is formed of at least one apex slat of the plurality of slats and the base (215) is formed of two co-planar base slats of the plurality of slats that are separated from the apex and also are laterally spaced apart from each other at about equal distances on either side of a center axis (240) that extends from a plane passing through the two base slats to a parallel plane passing through the at least one apex slat,
wherein the at least one apex slat and each of the two base slats are substantially parallel.

5. The inspection system of claim 4, wherein each of the plurality of slats is suspended above the conveyor.

6. The inspection system of claim 4, wherein the apex is directed toward an opening of the scanner.

7. The inspection system of claim 4, wherein the apex is directed away from an opening of the scanner.

8. The inspection system of claim 4, wherein the inspection system is an explosive detection system.

9. The inspection system of claim 4, wherein the inspection system is a medical inspection system.

* * * * *

UNITED STATES PATENT AND TRADEMARK OFFICE
CERTIFICATE OF CORRECTION

PATENT NO.       : 7,667,215 B2                                          Page 1 of 1
APPLICATION NO.  : 11/614095
DATED            : February 23, 2010
INVENTOR(S)      : Richard Oliver Hargrove, Jr.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 457 days.

Signed and Sealed this

Fourth Day of January, 2011

David J. Kappos
*Director of the United States Patent and Trademark Office*